(12) United States Patent
Hummel et al.

(10) Patent No.: US 11,665,464 B2
(45) Date of Patent: May 30, 2023

(54) DEVICE FOR SECURING COCHLEAR IMPLANT EXTERNAL TRANSMITTER

(71) Applicant: SYNAPS LLC, Lakewood, CO (US)

(72) Inventors: Ashley Hummel, Lakewood, CO (US); Mimi Lunde, Denver, CO (US); Paolo Grazioli, Centennial, CO (US); Andrew Reardon, Parker, CO (US)

(73) Assignee: SYNAPS LLC, Lakewood, CO (US)

( * ) Notice: Subject to any disclaimer, the term of this patent is extended or adjusted under 35 U.S.C. 154(b) by 107 days.

(21) Appl. No.: 16/901,793

(22) Filed: Jun. 15, 2020

(65) Prior Publication Data

US 2021/0387010 A1 Dec. 16, 2021

(51) Int. Cl.
| | |
|---|---|
| *H04R 1/10* | (2006.01) |
| *A61N 1/372* | (2006.01) |
| *A61N 1/36* | (2006.01) |
| *A61N 1/05* | (2006.01) |

(52) U.S. Cl.
CPC ......... *H04R 1/1066* (2013.01); *A61N 1/0541* (2013.01); *A61N 1/36038* (2017.08); *A61N 1/37229* (2013.01)

(58) Field of Classification Search
CPC ......... H04B 1/1607; A42B 1/041; A42B 1/08; A42B 3/32; A42B 1/241; A42B 3/08; A42B 7/00; H04R 1/1066
See application file for complete search history.

(56) References Cited

U.S. PATENT DOCUMENTS

| | | | | |
|---|---|---|---|---|
| 4,349,081 | A | * 9/1982 | Pepple | .................. H04R 25/00 181/130 |
| 4,918,757 | A | 4/1990 | Janssen | |
| 7,796,771 | B2 | 9/2010 | Calhoun | |
| 9,031,274 | B2 | * 5/2015 | Kasic, II | ................ H04R 25/60 381/151 |
| 10,172,406 | B2 | * 1/2019 | Olivares Velasco | ... G16H 40/67 |
| 10,631,793 | B1 | * 4/2020 | Luster | .................... A41D 20/00 |
| 2012/0143020 | A1 | * 6/2012 | Bordoley | ............. A61B 5/1114 600/383 |

(Continued)

OTHER PUBLICATIONS

Cochlear Softband Device, https://www.cochlear.com/us/en/home/products-and-accessories/baha-system/baha-softband-ancl-soundarc.

(Continued)

*Primary Examiner* — Quoc D Tran
(74) *Attorney, Agent, or Firm* — Shimokaji IP

(57) ABSTRACT

A device for securing an external transmitter of a cochlear implant to the head of the wearer. A pouch containing the external transmitter is secured using a plurality of straps coupled to a decorative shell worn on a person's head. The pouch and the decorative shell are designed to allow sound to pass unhindered from the environment to the inner ear. The plurality of straps are adjustable to allow precise placement of the external transmitter over the internal receiver. The external transmitter is also secured using a pouch coupled to a decorative shell. The external transmitter is further secured using a sealer coupled to the transmitter and further coupled to the head using an adhesive barrier. The sealer is made of a semi-transparent material. The device ensures that an external transmitter remains in place.

9 Claims, 7 Drawing Sheets

1A - Back View

1B - Side View

1C - Top View

1D - Adjustable Design

(56) References Cited

U.S. PATENT DOCUMENTS

| | | | |
|---|---|---|---|
| 2014/0049947 A1* | 2/2014 | Lombard | A41D 19/0157 362/105 |
| 2015/0223539 A1 | 8/2015 | Marco | |
| 2016/0302500 A1* | 10/2016 | Johnston | A42B 3/00 |
| 2019/0374776 A1* | 12/2019 | Mishra | A61N 1/3787 |
| 2020/0389742 A1* | 12/2020 | West | H02J 7/35 |
| 2021/0046311 A1* | 2/2021 | Brehm | A61N 1/36038 |
| 2021/0059343 A1* | 3/2021 | Carey | A42B 1/241 |
| 2021/0114862 A1* | 4/2021 | Crouthamel | B68B 5/06 |
| 2021/0236806 A1* | 8/2021 | Simons | A61N 1/36031 |

OTHER PUBLICATIONS

Cochlear Implant Headband—Ear Suspenders, https://www.etsy.com/listing/600258901/cochlear-implant-headband-ear-suspenders?ga_order=most_relevant&ga_search_type=all&ga_view_t.

Connector for Cochlear Softband, https://www.etsy.com/listing/585310688/connector-for-cochlear-baha4baha5-for?ga_order=most_relevant&ga_search_type=all&ga_view_type=gallery&ga.

Co-Amplify Cochlear Implant Hat, https://www.kickstarter.com/projects/343109221/coamplify-cochlear-implant-clothing-and-learning-t/description.

* cited by examiner

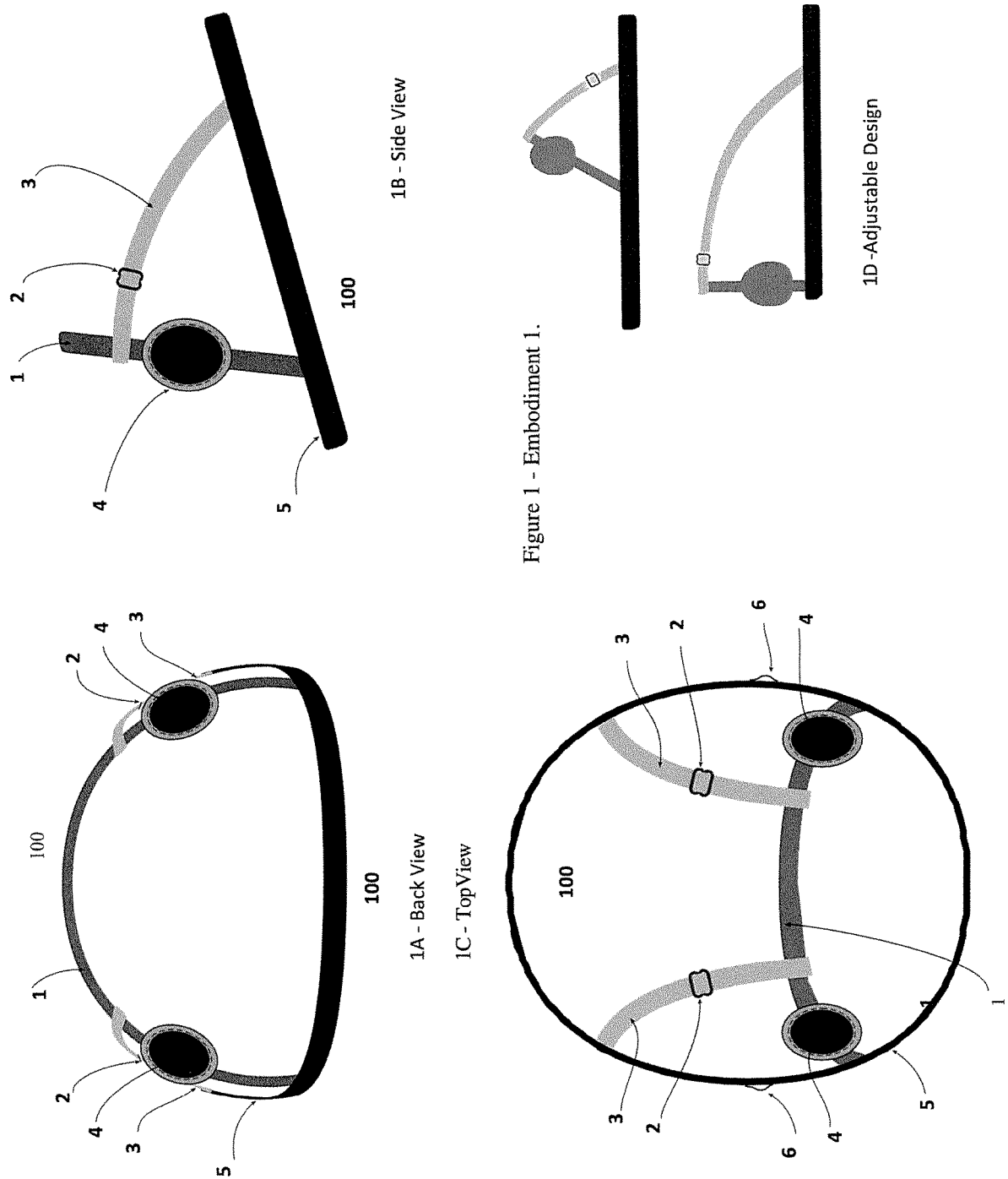

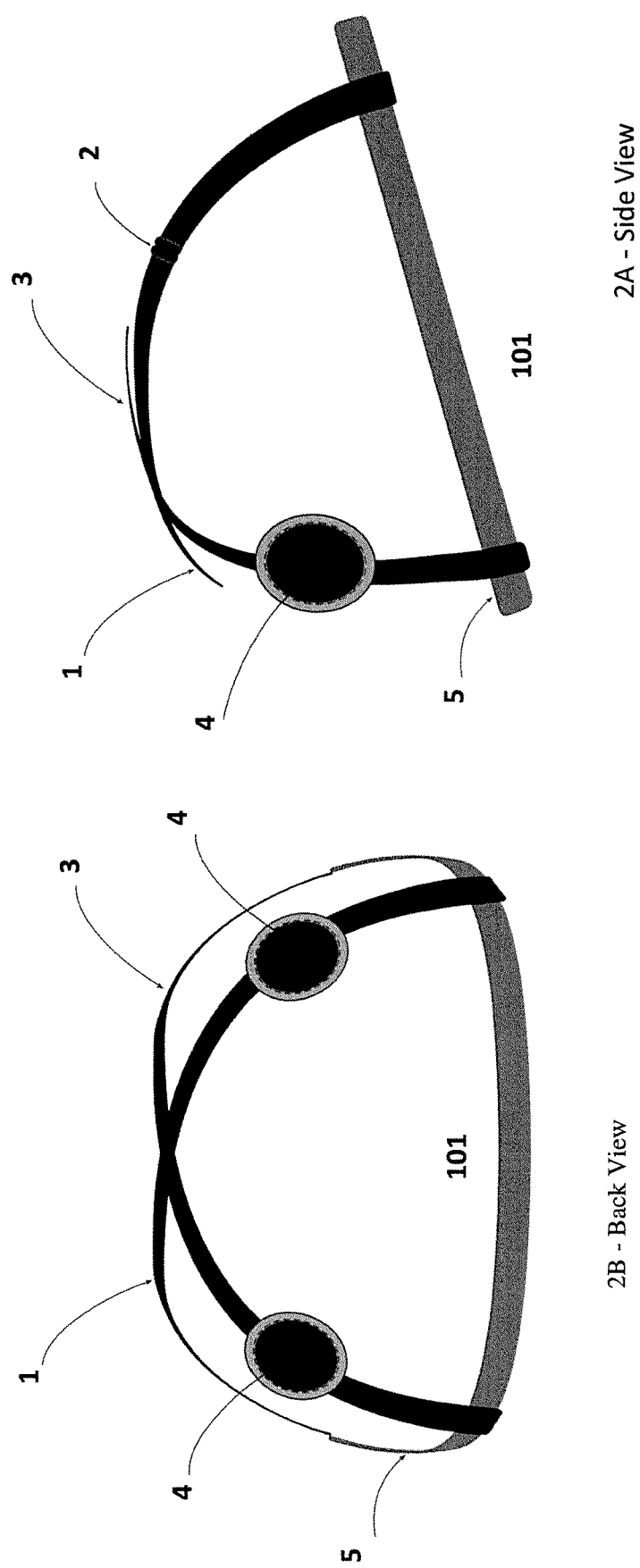
Figure 2 - Embodiment 2

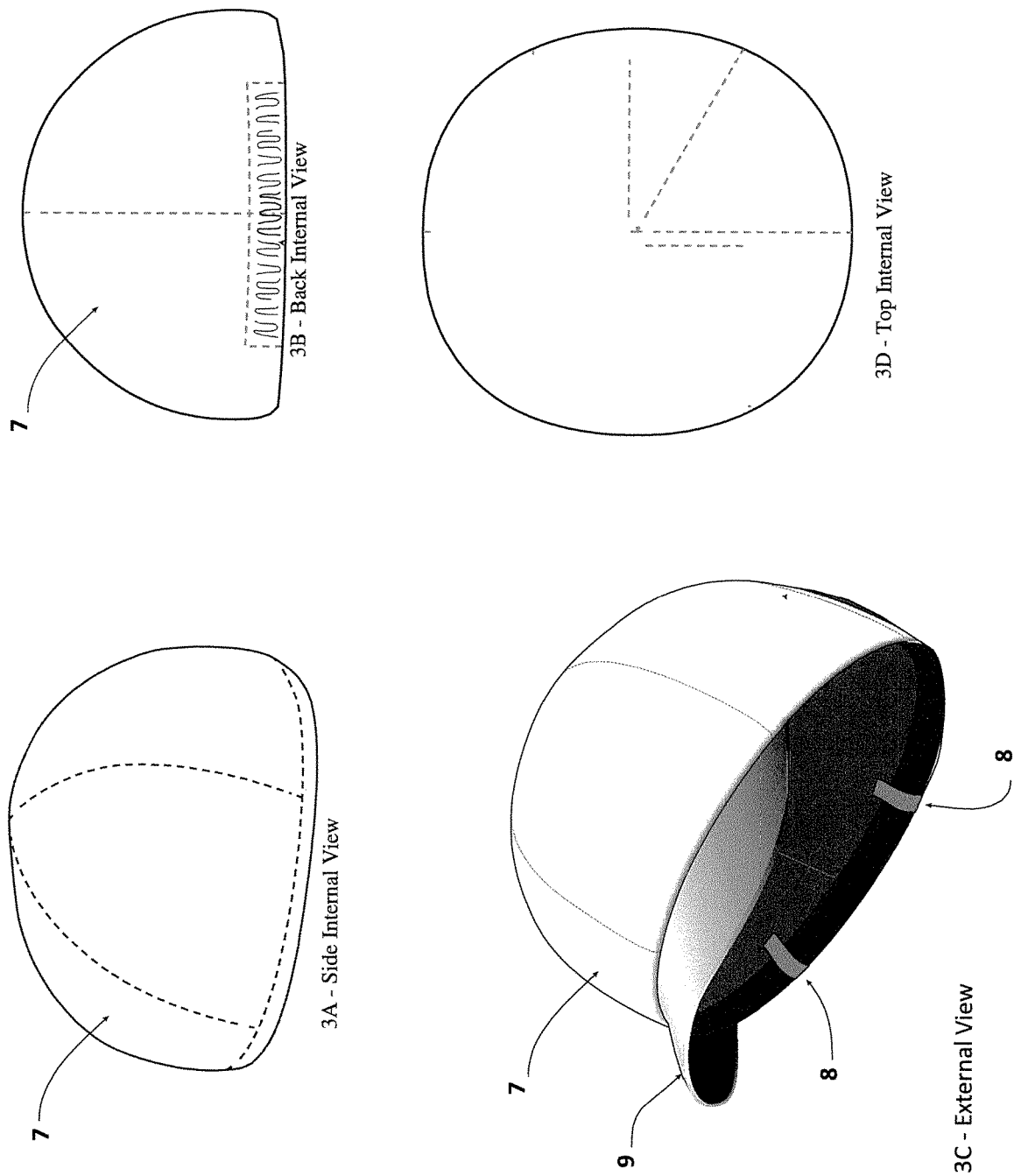
Figure 3 - Embodiment 1 & 2

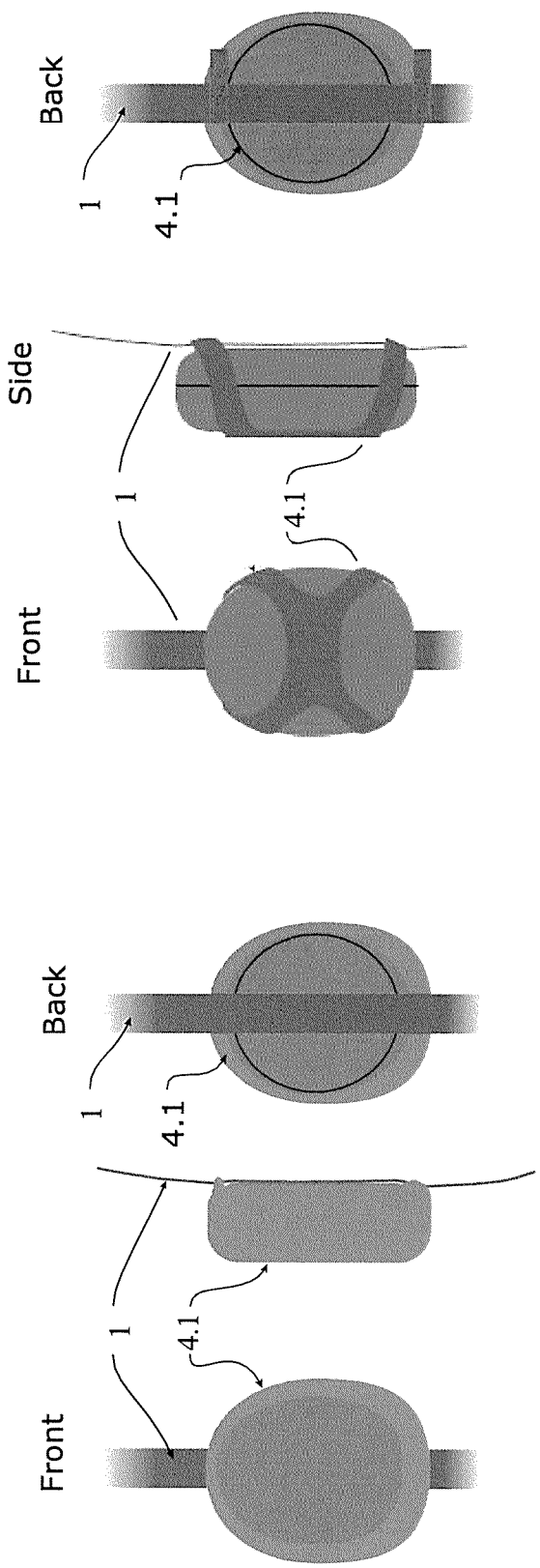
Figure 4 - Embodiment 1 & 2

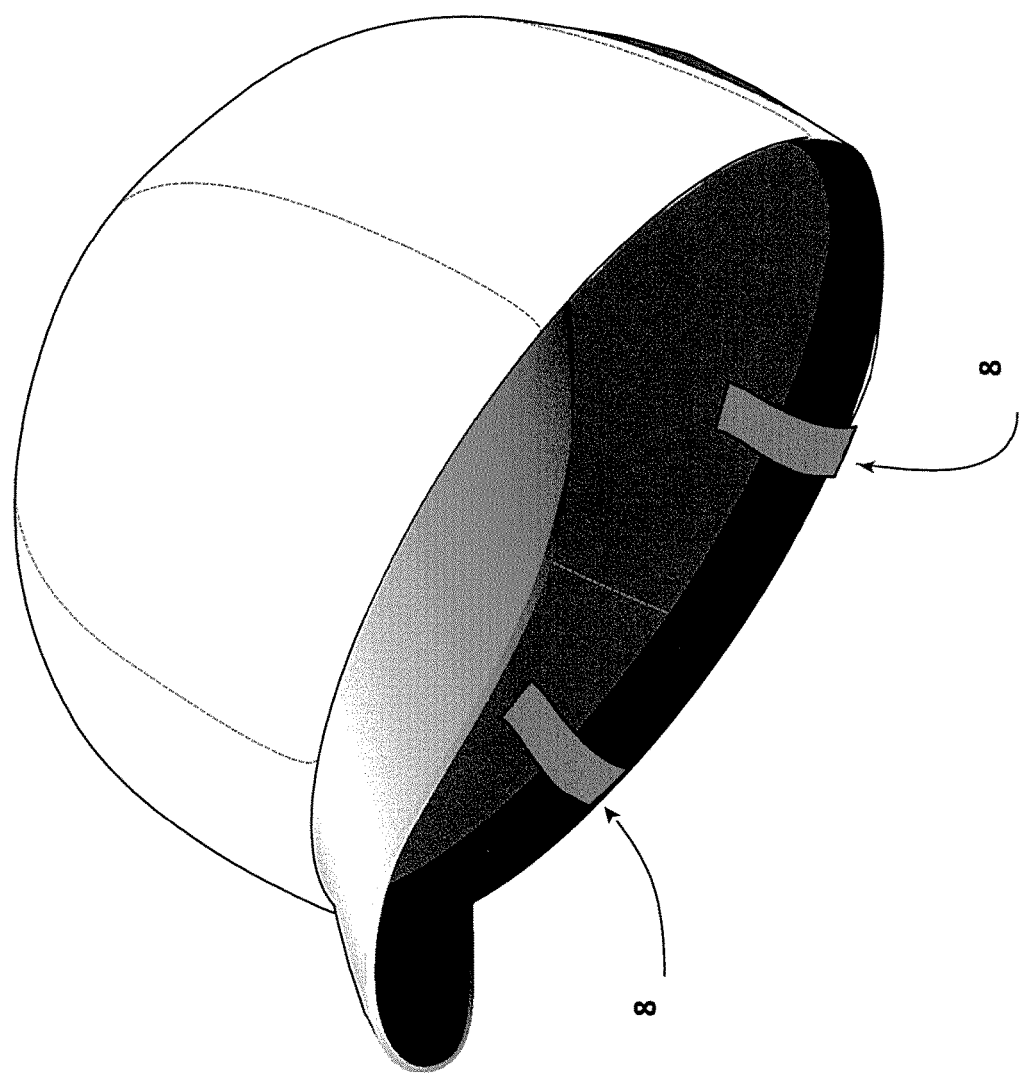
Figure 5 - Embodiment 1 & 2

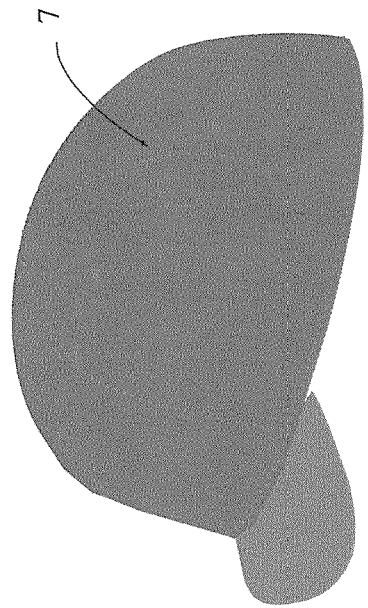
6B - Baseball Hat
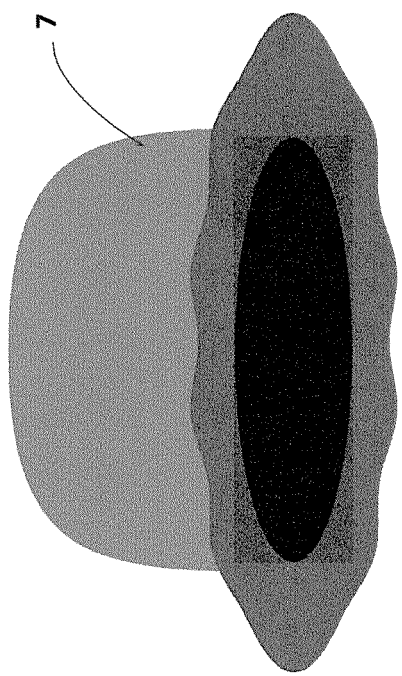
6A - Summer Hat
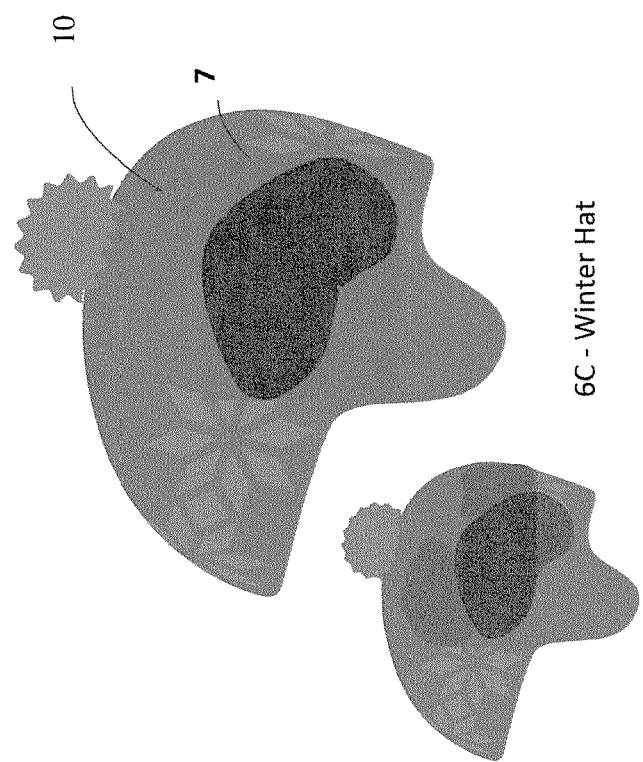
6C - Winter Hat
Figure 6 - Embodiment 1 & 2

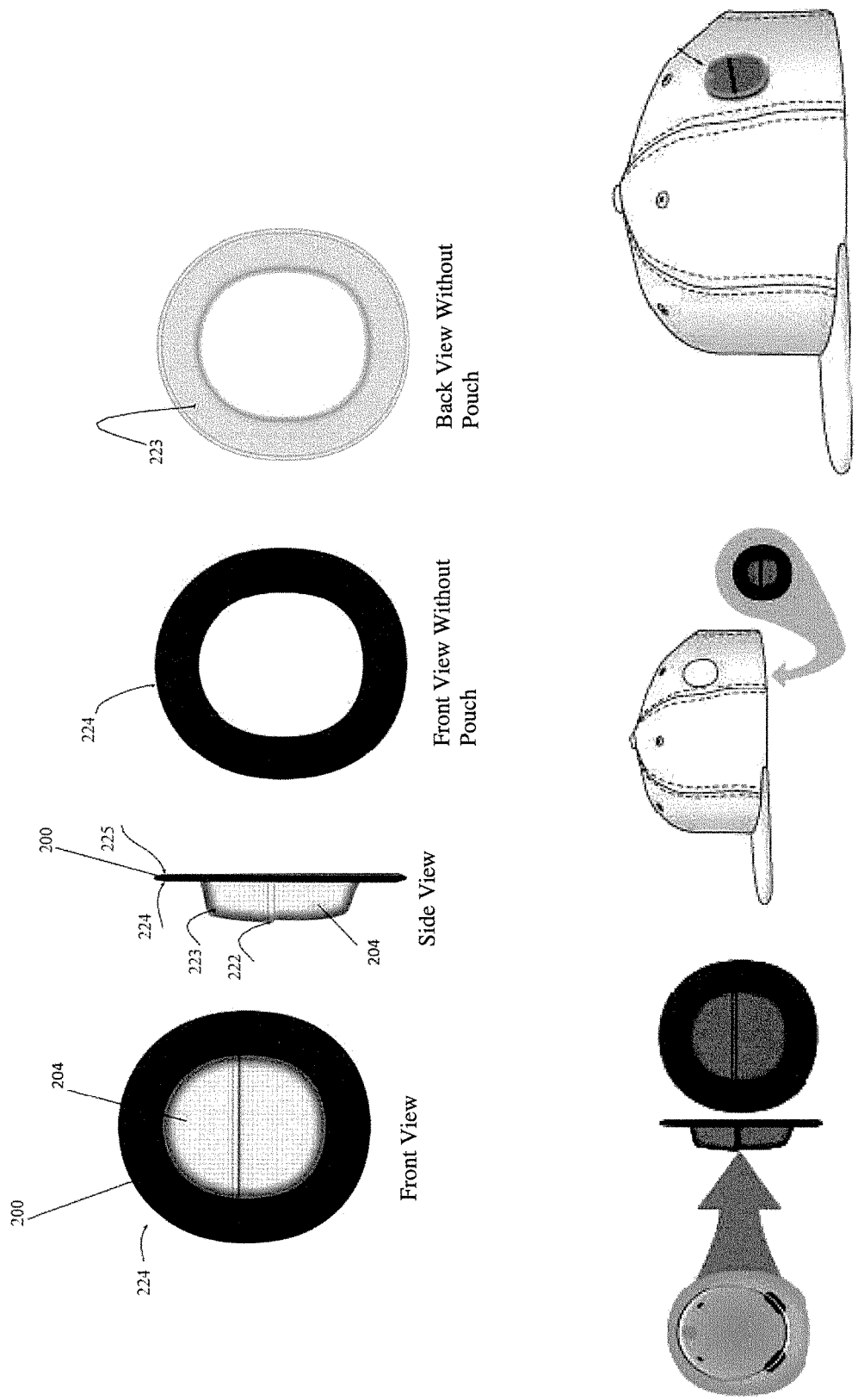
Figure 7 - Embodiment 4

DEVICE FOR SECURING COCHLEAR IMPLANT EXTERNAL TRANSMITTER

FIELD

The exemplary embodiments are related to the field of medical devices. More particularly, the exemplary embodiments relate to hearing aids.

BACKGROUND

Cochlear implant devices are a medical breakthrough for people who experience severe to profound nerve deafness. The devices function properly when an implanted receiver and electrode system is coupled with an externally worn microphone, sound processor and transmitter system. The internal and external components are held in place by a magnet. Young children who require the implant often require a weaker strength magnet to avoid developing painful welts on their soft, malleable heads. This will often cause the transmitter to fall off hundreds of times a day, leaving the child without the ability to hear and ultimately leading to further developmental difficulties. This conundrum is also difficult for the child's parents who must constantly monitor their hearing devices to ensure they are receiving the recommended hearing time each day.

SUMMARY

In the first and second exemplary embodiments, an acoustically transparent pouch, made of a material such as silicone or fabric, configured for coupling to an external transmitter of a cochlear implant and is further configured for coupling to a decorative shell, made of an acoustically-transparent material, using a plurality of straps.

In the third exemplary embodiment, a pouch, made of an acoustically transparent material, is configured for coupling to an external transmitter of a cochlear implant and is further configured for coupling to a decorative shell, using a fastener, such as a hook and loop fastener, or heat bonded adhesive.

BRIEF DESCRIPTION OF THE DRAWINGS

FIG. 1A shows a back view of a first exemplary embodiment of a cochlear implant securing device comprising a plurality of straps and pouches.

FIG. 1B shows a side view of the first exemplary embodiment of the cochlear implant securing device comprising the two pouches and the plurality of straps.

FIG. 1C shows a top view of the first exemplary embodiment of the cochlear implant securing device comprising the pouches and the plurality of straps.

FIG. 1D shows the full adjustability of the first exemplary embodiment of the cochlear implant securing device comprising a pouch and a plurality of straps.

FIG. 2A shows a side view of a second exemplary embodiment of the cochlear implant securing device comprising a plurality of straps and a pouch.

FIG. 2B shows a back view of the second exemplary embodiment of the cochlear implant securing device having the pouches and the plurality of straps.

FIG. 3A shows a side, internal view of an exemplary decorative shell. The dashed lines show the decorative shell in a three-dimensional orientation.

FIG. 3B shows a back, internal view of the exemplary decorative shell that may be adjustable to the head of the wearer.

FIG. 3C shows a side, external view of the exemplary decorative shell. In this embodiment, the decorative shell is a baseball-style hat.

FIG. 3D shows a top, internal view of the exemplary decorative shell.

FIG. 4A shows a front view, a side view, and a back view of the pouch configured for coupling to the plurality of straps and an external transmitter of a cochlear implant according to the first and second exemplary embodiments.

FIG. 5 shows an exemplary fastener of the first and second exemplary embodiments of the cochlear implant securing device to couple to the decorative shell.

FIG. 6 shows three exemplary embodiments of the decorative shell configured for coupling to the plurality of straps.

FIG. 7 shows a front view, back view, and a side view of a third exemplary embodiment of a cochlear implant securing device.

DETAILED DESCRIPTION

The exemplary embodiments may be further understood with reference to the following descriptions and the related appended drawings, wherein like elements are provided with the same reference numerals. The exemplary embodiments are related to a device for securing an external cochlear implant to the head of the wearer using a pouch configured for coupling to a decorative shell.

A cochlear implant device consists of two main components. The first component is an external transmitter that contains a microphone and a sound processor to gather sounds from the surrounding environment. The second component is a sound-receiving device that is implanted into the head of the wearer. Once a sound is picked up by the external transmitter, it is passed to the internal receiver, processed, and an electrical current is passed to the inner ear where a sound is created.

The external transmitter is coupled to the internal sound receiver using a magnet. This connection ensures the cochlear implant remains in place and sound processing is completed. In young children, the magnet is considerably weaker than ones used in adults, which helps prevent welts from developing on their malleable heads. However, because the magnet is weak, the external transmitter will often fall or be knocked off the child's head and cause auditory and speech development problems. The cochlear implant securing device, as described herein, functions to secure the transmitter to the internal receiver allowing for proper sound transmission.

FIG. 1A shows a back view of a first exemplary embodiment of a cochlear implant securing device 100 comprising a plurality of straps 1, 3, 5, and pouches 4. The pouches 4 are designed to house the external transmitter of the cochlear implant device. The pouches 4 are specifically designed to be acoustically transparent, which is facilitated by being made of a material such as silicone or fabric. This design allows for unhindered sound transmission. The plurality of straps 1, 3, 5, are configured to be coupled to a head of a user (i.e., worn by the user). In this example, the pouches 4 are coupled to the strap 1 in a manner to ensure that the pouches 4 with the transmitters remain connected to the internal receiver of the cochlear implant device. However, one skilled in the art will understand that the pouches 4 may be coupled to any of the straps 1, 3, 5 and the placement of the pouches may depend on the placement of the implant in the user's head.

The plurality of straps 1, 3, 5, are made of a non-slip elastic material, which allows the embodiment to fit many different size heads. The plurality of straps comprises a first strap 5 configured to wrap around the head of the wearer, a second strap 1 attached at a first end and a second end to the first strap 5 and two third straps 3 coupled to the first strap 5 and the second strap 1. The third straps 3 are coupled to the second strap 1 at a first end using a tight-fitting loop system. The tight-fitting loop system allows universal positioning of the plurality of straps 1, 3, 5, and the pouch 4 to ensure that the external transmitter can be connected to the internal receiver of the cochlear implant for all users.

FIG. 1B shows a side view of the first exemplary embodiment of the cochlear implant securing device 100 comprising the two pouches 4 and the plurality of straps 1, 3, 5. In this embodiment, two pouches 4 are utilized for a person with bilateral hearing impairments. The cochlear implant securing device 100 may also be designed with a one pouch 4 arrangement for a person with unilateral hearing impairments. This view shows the first strap 5 coupled to the second strap 1 and the third strap 3. The third strap 3 is coupled to the second strap 1 at a first end using a tight-fitting loop system. The third strap 3 also includes a first slider 2 that may be used to vary the length of the third strap 3 and position the pouch 4 containing the external transmitter directly over the internal receiver of the cochlear implant for proper sound transmission.

FIG. 1C shows a top view of the first exemplary embodiment of the cochlear implant securing device 100 comprising the pouches 4 and the plurality of straps 1, 3, 5. This view shows the first strap 5 coupled to the second strap 1 and two third straps 3. The two third straps 3 are coupled to the second strap 1 at a first end using a tight-fitting loop system. In this embodiment, two third straps 3 are utilized for coupling to two pouches 4. The two third straps 3 allow for people with bilateral hearing disabilities to have both external transmitters securely fastened to their head. The two third straps 3 have a first slider 2, capable of shortening the two third straps 3.

FIG. 1D shows the configuration of the plurality of straps 1, 3, 5 and movement of the pouch 4 are completely adjustable, covering roughly a 2½ inch radius on a child's head, to accommodate each individual cochlear implant location. Adjustments can be made by sliding straps 1 and 3, lengthening or shortening slider 2 and by moving pouch 4 up or down.

FIG. 2A shows a side view of a second exemplary embodiment of the cochlear implant securing device 101 comprising a plurality of straps 1, 3, 5 and a pouch 4. The cochlear implant securing device 101 is similar to the cochlear implant securing device 100 described with reference to FIGS. 1A-D. The difference between the two exemplary embodiments is the number, orientation and position of the straps 1, 3, 5. This should make it clear that the exact number, orientation and position of the straps may be modified within the scope of the exemplary embodiments, as long as the arrangement secures the straps to the head of the user and the pouch in a position where the external transmitter is in the correct location with respect to the internal receiver.

This view shows the first strap 5 coupled to the second strap 1 and the third strap 3. The third strap 3 is coupled to the second strap 1 using tight-fitting loop system. In this embodiment, the plurality of straps 1, 3, 5, can be adjusted to position the pouch 4 on the internal receiver of the cochlear implant device.

FIG. 2B shows a back view of the second exemplary embodiment of the cochlear implant securing device 101 having the pouches 4 and the plurality of straps 1, 3, 5. This embodiment shows two pouches 4 for bilateral hearing disabilities. This view shows the first strap 5 coupled to the second strap 1 and two third straps 3. The third straps 3 are coupled to the first strap 1, which permits universal adjustment of the pouches 4 over the internal receiver of the cochlear implant device.

FIG. 3A shows a side, internal view of an exemplary decorative shell 7. The dashed lines show the decorative shell in a three-dimensional orientation. The decorative shell 7 may be constructed of an acoustically transparent material, which allows unhindered sound transmission from the surrounding environment, through the transmitter, to the inner ear. Without this material, the sound may be muffled, and the wearer may suffer further developmental complications. The dashed lines show the decorative shell in a three-dimensional orientation.

FIG. 3B shows a back, internal view of the exemplary decorative shell 8 that may be adjustable to the head of the wearer. The dashed lines show the decorative shell in a three-dimensional orientation.

FIG. 3C shows a side, external view of the exemplary decorative shell 7. In this embodiment, the decorative shell is a baseball-style hat. In the example shown, the decorative shell 7 is configured for coupling to the plurality of straps using a fastener 8 and further comprises a brim 9. The exemplary fastener 8 is a loop-type fastener wherein loop is positioned on the decorative shell 7 and configured for coupling to the first strap 5. Those skilled in the art will understand that other types of fasteners may also be used to secure the decorative shell 7 to the cochlear implant securing device 100, 101 such as, snaps, hook and loop fasteners, buttons, etc.

FIG. 3D shows a top, internal view of the exemplary decorative shell 7. In the example shown, the decorative shell 7 is configured for coupling to the plurality of straps using a loop fastener 8. The dashed lines show the decorative shell in a three-dimensional orientation.

FIG. 4A shows a front view, a side view, and a back view of the pouch 4 coupled to the second strap 1. The second strap 1 is configured to couple to the pouch 4 using retention strap 4.1. The retention strap 4.1 is shown in two configurations in FIG. 4A. These configurations are designed to secure the second strap 1 to the pouch 4, while covering a minimal surface area of the pouch 4. This helps reduce interference of sound transmission from the external environment to the inner ear. In this embodiment, the retention strap 4.1 is constructed from a thermoplastic elastomer or fabric, which expands to allow the pouch 4 to slide into the strap and closes to hold the pouch 4 in place.

FIG. 5 shows an exemplary fastener 8 of the first and second exemplary embodiments of the cochlear implant securing device 100, 101 to couple to the decorative shell 7. The fastener 8 is shown as a loop-type fastener configured for coupling the decorative shell 7 to the first strap 5 of the plurality of straps. However, as described above, other types of fasteners may be used.

FIG. 6 shows three exemplary embodiments of the decorative shell 7 configured for coupling to the plurality of straps. In FIG. 6A, the decorative shell 8 is a summer hat. In FIG. 6B, the decorative shell 8 is a baseball cap. In FIG. 6C, the decorative shell is a fleece winter hat; having an internal layer of acoustically transparent material 7 and an external layer of fleece or other materials 10. In each of the embodiments, the decorative shell 7 is made of an acoustically-transparent material. This material allows unobstructed sound transmission from the external environment to the inner ear through the cochlear implant device.

FIG. 7 shows a front view and a side view of a third exemplary embodiment of a cochlear implant securing device 200. In this exemplary embodiment, there are no straps to attach to the user's head. Rather, a pouch 204 is configured to couple to a decorative shell 208 using a fastener or a head-bonded adhesive. In this example, the fastener may be a hook 224 and loop 225 style-fastener. In this exemplary embodiment, a hole, approximately the size of the pouch 204, is cut out of the decorative shell 208 in the area above the internal receiver of the cochlear implant device. The hook fastener 224 is then attached to the decorative shell 208 using an adhesive glue. The pouch 204 with the loop fastener 225 is then coupled to the hook fastener 224. The pouch 204 is made of an acoustically transparent material 223 to allow sound to pass unhindered from the external environment to the inner ear. The pouch 204 has a closure 222, which ensures that the external transmitter of a cochlear implant remains attached to the internal receiver. FIG. 7 also shows a front and back view of the exemplary hook 224 and loop 225 style-fastener for coupling the pouch 204 and the decorative shell 208. It should be appreciated that in this exemplary embodiment, the decorative shell 208 may not be constructed of an acoustically transparent material because of the hole that is cut in the decorative shell 208.

Although this application described various embodiments each having different features in various combinations, those skilled in the art will understand that any of the features of one embodiment may be combined with the features of the other embodiments in any manner not specifically disclaimed or which is not functionally or logically inconsistent with the operation of the device or the stated functions of the disclosed embodiments.

It will be apparent to those skilled in the art that various modifications may be made in the present disclosure, without departing from the spirit or the scope of the disclosure. Thus, it is intended that the present disclosure cover modifications and variations of this disclosure provided they come within the scope of the appended claims and their equivalent.

What is claimed is:

1. A device, comprising:
   a pouch configured to couple to an external transmitter of a cochlear implant comprising a magnet, microphone, and sound processor;
   a plurality of straps, wherein the plurality of straps comprises a first strap configured to wrap around a circumference of the head of the wearer, a second strap attached at a first end and a second end to the first strap, a third strap movably coupled to the first strap and slidably coupled along the second strap, wherein the pouch is configured to couple to the second strap and wherein the third strap has a first slider to adjust a length of the third strap and to thereby move the second strap to position the pouch over an internal receiver of the cochlear implant; and
   a decorative shell configured to couple to the plurality of straps and worn on a head of a wearer, wherein the decorative shell is configured to couple to the first strap.

2. The device of claim 1, wherein the decorative shell comprises an acoustically transparent material.

3. The device of claim 1, wherein the pouch is made acoustically transparent by using silicone.

4. The device of claim 1, wherein the pouch comprises an opening allowing the second strap to pass through the pouch.

5. The device of claim 1, further comprising:
   a retention strap configured to secure the pouch to the second strap.

6. The device of claim 1, wherein the pouch comprises a plurality of pouches.

7. The device of claim 1, wherein the third strap is coupled to the second strap at a first end using a tight-fitting loop allowing the third strap to slide with respect to the second strap.

8. The device of claim 1, wherein the decorative shell is a hat.

9. The device of claim 8, wherein the hat is adjustable to the head of the wearer.

\* \* \* \* \*